(12) United States Patent
Kim et al.

(10) Patent No.: US 8,426,620 B2
(45) Date of Patent: Apr. 23, 2013

(54) PRODUCTION METHODS OF FURAN FATTY ACIDS

(75) Inventors: Hak ryul Kim, Daegu (KR); Joel B. Ellamar, Daegu (KR)

(73) Assignee: Kyungpook National University Industry-Academic Cooperation Foundation (KR)

( * ) Notice: Subject to any disclaimer, the term of this patent is extended or adjusted under 35 U.S.C. 154(b) by 13 days.

(21) Appl. No.: 13/191,855

(22) Filed: Jul. 27, 2011

(65) Prior Publication Data

US 2012/0302774 A1    Nov. 29, 2012

(51) Int. Cl.
*C07D 307/02* (2006.01)
(52) U.S. Cl.
USPC .......................................... 549/499; 549/561
(58) Field of Classification Search .................. 549/499, 549/561
See application file for complete search history.

(56) References Cited

PUBLICATIONS

Youji Okada, et al., "Antioxidant Effect of Naturally Occurring Furan Fatty Acids on Oxidation of Linoleic Acid in Aqueous Dispersion," J. Am. Oil Chem. Soc., Nov. 1990, vol. 67, No. 11, pp. 858-862.*
Robert L. Glass, et al., "Furanoid Fatty Acids from Fish Lipids," Lipids, 1975, vol. 10, pp. 695-702.
G. L. Glass, et al., New Series of Fatty Acids in Northern Pike (*Esox indus*), Lipids, 1974, vol. 9, pp. 1004-1008.
Frank D. Gunstone, et al., "The Component Acids of Lipids from Marine and Freshwater Species with Special Reference to Furan-Containing Acids," J. Sci. Food Agric., 1978, vol. 29, pp. 539-550.
Kerstin Hannemann, et al., "The Common Occurrence of Furan Fatty Acids in Plants," Lipids, 1989, vol. 24, No. 4, pp. 296-298.
Kasuo Ishii, et al., "Studies on Furan Fatty Acids of Salmon Roe Phospholipids," J. Biochem., 1988, vol. 103, pp. 836-839.
Toru Ota, et al., "Furan Fatty Acids in the Lipids of the Cresthead Flounder," Nippon Suisan Gakkaishi, 1992, vol. 58, No. 4, pp. 721-725.
Kazuo Ishii, et al., "Effects of Phosphatidylcholines Containing Furan Fatty Acid on Oxidation in Multilamellar Liposomes," Chem. Pharm. Bull., 1989, vol. 37, No. 5, pp. 1396-1398.
Youji Okada, et al., "Hydroxy Radical Scavenging Activity of Naturally Occurring Furan Fatty Acids," Biol. Pharm. Bull., 1996, vol. 19, No. 12, pp. 1607-1610.
Rober L. Glass, et al., "The Occurrence and Distribution of Furan Fatty Acids in Spawning Male Freshwater Fish," Lipids, 1977, vol. 12, No. 10, pp. 828-836.
Gerhard Spiteller, "Furan fatty acids:Occurences, synthesis, and reactions. Are furan fatty acids responsible for the cardioprotective effects of a fish diet?" Lipids, 2005, vol. 40,I No. 8, pp. 755-771.
Andreas Batna, et al., "Oxidation of Furan Fatty Acids by Soybean Lipoxygenase-1 in the Presence of Linoleic Acid," Chem. Phys. Lipids, 1994, vol. 70, pp. 179-185.

Joachim Jandke, et al., "Über das Verhalten von F-Sauren bei der Oxidation mit Lipoxydase in Anwesenheit von SH-haltigen Verbindungen," Liebigs Ann. Chem., 1988, pp. 29-34.
Rolf Schodel, et al., "Uber die Strukturaufklärung von (Hydroxy-oxo-cyclopentenyl) alkansauren, den Aldolkondensationsprodukten von Dioxoen carbonsäuren aus Rinderleber," Helv. Chim. Acta, 1985, vol. 68, pp. 1624-1634.
Josef Scheinkonig, et al., "Methylation of the β-Positions of the Furan Ring in F-Acids," Biochim. Biophys. Acta, 1995, vol. 1254, pp. 73-76.
Volker Puchta, et al., "F-Säuren: Eine bisher unbekannte Komponente der Phospholipide des Humanblutes," Liebigs Ann. Chem., 1988, pp. 25-28.
In-Ae Chang, et al., "Production of 7,10-dihydroxy-8(E)-octadecenoic acid from triolein via lipase induction by *Pseudomonasa eruginosa* PR3," Appl. Microbiol. Biotechnol., 2007, vol. 74, pp. 301-306.
Dektas Tepe, et al., "Antioxidant activity of the essential oil and various extracts of *Nepeta flavida* Hub-Mor from Turkey," Food Chem., 2007, vol. 103, pp. 1358-1364.
Marcel S. F. Lie Ken Jie, et al., "A Novel method for the introduction of a methyl group into the furan ring of a 2,5-disubstituted C18 furanoid fatty ester via a malonic acid function," Lipids, 1991, vol. 26, No. 10, pp. 837-842.
M. S. F. Lie Ken Jie, et al., "Fatty acids: Part XVI. The synthesis of all isomeric C18 furan-containing fatty acids," Chem. Phys. Lipids, 1978, vol. 21, pp. 275-287.
M. Alaiz, et al., "Synthesis of 9,12-epoxy octadeca-9,11-dienoic acid," Chem. Phys. Lipids, 1988, vol. 48, pp. 289-292.
David C. White, et al., "Phospholipid furan fatty acids and ubiquinone-8:lipids biomarkers that may protect *Dehalococcoides* strains from free radicals," Appl. Environ. Microbiol., Dec. 2005, vol. 71, No. 12, pp. 8426-8433.
Hans Gunther Wahl, et al., "Identification of Furan Fatty Acids in Human Blood Cells and Plasma by Multi-dimensional Gas Chromatography—Mass Spectrometry," J. Chromatogr. A 1995, vol. 697, pp. 453-459.
L. J. Morris, et al., "A Unique Furanoid Fatty Acid from Exocarpus Seed Oil." Tetrahedron Letters, 1966, pp. 4249-4253, No. 36.
Gustav Graff, et al., "Inhibition of Blood Platelet Aggregation by Dioxo-ene Compounds." Biochimmica et Biophysica Acta, 1984, pp. 143-150, vol. 799.
Claus Fuchs, et al., "Iron Release from the Active Site of Lipoxygenase," Z. Naturforsch., 2000, pp. 643-648, vol. 55.
Barry Halliwell, et al., "Role of Free Radicals and Catalytic Metal Ions in Human Disease: An Overview," Methods Enzymol., 1990, pp. 1-85, vol. 186.

* cited by examiner

*Primary Examiner* — Deborah D Carr
(74) *Attorney, Agent, or Firm* — Cantor Colburn LLP

(57) ABSTRACT

Disclosed is a method for preparing a furan fatty acid, more particularly a method for preparing a furan fatty acid by heat-treating 7,10-dihydroxy-8(E)-octadecenoic acid (DOD) in hexane. The present disclosure provides a simple method for producing 7,10-EODA from a dihydroxyl fatty acid precursor. Considering the difficulties in purifying natural furan fatty acids because of easy attack by peroxyl radicals and small quantity and the complicated multiple steps for chemical synthesis, the present disclosure provides a useful way to produce the biologically activity F-acid cost-effectively in large scale.

8 Claims, 6 Drawing Sheets

PRODUCTION METHODS OF FURAN FATTY ACIDS

CROSS-REFERENCE TO RELATED APPLICATIONS

This application claims priority under 35 U.S.C. §119 to Korean Patent Application No. 10-2011-0049750, filed on May 25, 2011 in the Korean Intellectual Property Office, the disclosure of which is incorporated herein by reference in its entirety.

TECHNICAL FIELD

The present disclosure relates to a method for preparing a furan fatty acid, and in particular, to a method for preparing a furan fatty acid including heat-treating 7,10-dihydroxy-8(E)-octadecenoic acid (DOD) in hexane.

BACKGROUND ART

Furan fatty acids (F-acids) are a large group of fatty acids characterized by a furan ring, which carries at one α-position an unbranched fatty acid chain with 9, 11, or 13 carbon atoms and at the other α-position a short straight-chain alkyl group with 3 or 5 carbon atoms (1). Mostly two β-positions of the furan ring are substituted by either one or two methyl residues or other group. F-acid without any substitutions on both β-positions of the furan ring was also found in the seed oil of *Exocarpus cupressiformis* (2). F-acids are widely distributed in nature as trace components of plants, fishes, amphibians, reptiles, microorganisms and mammals including human (1, 3-7).

Although the biological role of F-acids in the biological system is not fully understood, it has been pointed out that F-acids can be involved in various important biological functions acting as antioxidant, antitumoral and antithrombotic (8-10). In some fishes F-acids comprised up to 25% of the acids in the liver lipids and accumulated during the spawning season indicating possible correlation between F-acids and the fertilization process (11). The correlation between consumption of fish rich in F-acid and protection against coronary heart disease mortality has been confirmed in several studies (12). F-acid has also been reported to have inhibitory effects on blood platelets aggregation (9) and to have potential antitumor activity (8). F-acids were found to prevent oxidation of linoleic acid (13) and act as antioxidants in plants (14). Some studies demonstrated that F-acids underwent oxidation by ring opening to form dioxoenes (15-16) in the presence of linoleic acid as co-substrate demonstrating that F-acid acted as a radical scavenger (17-18).

Biosynthesis of F-acids are complicated and quite different from sources. The biogenetic precursor of the most F-acids is known to be linoleic acid. It was recognized that plants synthesized the basic skeleton of F-acids from different sources (19). However, study with the radio-labeled feeding to fish indicated that fish synthesized neither the alkyl side chain nor the furan ring of F-acids (1). Therefore F-acids in fish were considered to be originated from diet, especially algae. Consequently F-acids are introduced into human body through the diet like vegetables and fishes. Diet-derived F-acid are incorporated into the tissue and blood of mammals, especially into phospholipids (20) where they might act as radical scavengers resulting into inhibition of blood platelet aggregation (9).

These reports indicated that F-acid could be an essential nutritional factor for mammals and could be used as an active component of functional food. However, no matter what biological sources of F-acids were, biosynthesis of F-acids required multistep reactions due to the formation of furan ring and the different alkyl substituents. Accordingly, chemical synthesis of F-acids required complicated multistep reactions and chemical catalysts causing difficulties and high costs for industrial application.

Recently we have produced 7,10-dihydroxy-8(E) octadecenoic acid (DOD) from vegetable oil containing oleic acid by microbial conversion (21). DOD is a dihydroxy monoenoic $C_{18}$ fatty acid uniquely carrying two hydroxyl groups at carbon 7 and 10 and a trans double bond between carbon 8 and 9. Based on unique structural feature, it is highly plausible to modify DOD molecules by intra- or intermolecular interaction via chemical or physical ways. In our constant efforts to modify DOD for biological and industrial applications, we developed a simple way to produce a novel biologically active F-acid from DOD through one-step heat treatment.

SUMMARY

The present disclosure is directed to providing a method for preparing a novel, biologically active furan fatty acid through a one-step heat treatment process using 7,10-dihydroxy-8(E)-octadecenoic acid prepared from vegetable oil by microbial conversion.

The present disclosure is also directed to providing a novel furan fatty acid prepared by the method.

The present disclosure is also directed to providing an antioxidant containing the furan fatty acid.

In one general aspect, the present disclosure provides a method for preparing a furan fatty acid, including: mixing 7,10-dihydroxy-8(E)-octadecenoic acid (DOD) with hexane; and heat-treating the resulting mixture.

The 7,10-dihydroxy-8(E)-octadecenoic acid is represented by Chemical Formula 1:

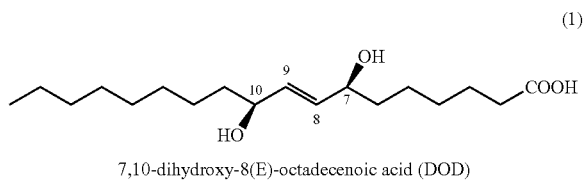 [SMILES: CCCCCCCC[C@H](O)/C=C/[C@@H](O)CCCCCC(=O)O]

7,10-dihydroxy-8(E)-octadecenoic acid (DOD)

The 7,10-dihydroxy-8(E)-octadecenoic acid may be synthesized chemically or produced by microorganisms. Specifically, it may be produced by the microorganism *Pseudomonas aeruginosa* using oleic acid or vegetable oil containing oleic acid as substrate.

The microorganism may be any bacterium belonging to *Pseudomonas aeruginosa*. Specifically, it may be *Pseudomonas aeruginosa* PR3 (NRRL strain B-18602).

The *Pseudomonas aeruginosa* PR3 is deposited in the Agricultural Research Service Culture Collection (Peoria, Ill., USA) with under Accession No. NRRL B-18602.

7,10-Dihydroxy-8(E)-octadecenoic acid is a hydroxy fatty acid having two hydroxyl groups on a $C_{18}$ fatty acid chain, each at carbon 7 and 10, and having a trans double bond between carbon 8 and 9.

The substrate used to produce the 7,10-dihydroxy-8(E)-octadecenoic acid may be oleic acid or any natural vegetable oil containing oleic acid. Specifically, olive oil, safflower seed oil, soybean oil, corn oil, sesame oil, *perilla* oil, grape seed oil, hot pepper seed oil, canola oil, sunflower oil, Korean melon seed oil, rapeseed oil, rice bran oil, or the like may be used.

The natural vegetable oil may be prepared by solvent extraction or pressed extraction that have been traditionally employed to extract oil from natural plant seeds or fruits or may be easily purchased from the market.

Furan fatty acids (F-acids) are a large group of fatty acids characterized by a furan ring. They are widely distributed in the nature as trace components in plants, fish, amphibians, reptiles, microorganisms, and mammals including human. As described in the Background section, furan fatty acids are important essential nutritional factors for mammals and can be used as active components in functional foods.

The furan fatty acid according to the present disclosure is 7,10-epoxy-octadeca-7,9-dienoic acid (7,10-EODA). Most of the previously known furanoid fatty acids are found in trace amounts in fish. Mostly, the furan ring is substituted by one or two methyl residues. The length of the side chain is various. It is also known to be contained in human blood in trace quantity. One with no methyl residue is not known to occur naturally and it is reported that a small amount can be produced as intermediate when linoleic acid is treated with lipoxygenase. However, the resulting furanoid fatty acid is different in the position of the furan ring from that provided by the present disclosure. That is to say, it has an epoxy structure carbon 10 and 13. As such, the novel furanoid fatty acid presented in the present disclosure is a new substance that has never been reported.

When mixing DOD with hexane, the mixing ratio of DOD and hexane may be determined appropriately. For efficient mixing with DOD and production of the desired product, hexane may be used in an amount corresponding to 0.001-1000 times that of DOD. Specifically, 10-1000 μL of hexane may be used per 10 mg of DOD.

When preparing the furan fatty acid according to the present disclosure, the heat treatment may be performed at 30-150° C. for 1-150 hours. Specifically, it may be performed at 90° C. for 36-96 hours. According to experiments performed by the inventors, 7,10-EODA is produced with very high yield of 70-80% at temperatures between 85° C. and 95° C., and increasing the reaction time gives the same result as that of elevating the reaction temperature. The production of 7,10-EODA started at 12-96 hours and reached maximum at 36-96 hours (see FIGS. 6 and 7).

In another general aspect, the present disclosure provides 7,10-epoxy-octadeca-7,9-dienoic acid prepared by heat-treating 7,10-dihydroxy-8(E)-octadecenoic acid (DOD) in hexane.

The furan fatty acid prepared in accordance with the present disclosure is 7,10-epoxy-octadeca-7,9-dienoic acid (7,10-EODA). Whereas most of the naturally occurring furanoid fatty acids have one or two methyl groups on the furan ring, the furan fatty acid of the present disclosure does not have a methyl group. Also, the method for preparing a furan fatty acid according to the present disclosure allows preparation of the novel furan fatty acid from DOD through a one-step heat treatment process, without using a chemical catalyst.

The inventors of the present disclosure have found out for the first time that the novel, physiologically active compound can be prepared from DOD through heat treatment. Chemical analysis of the purified product revealed that the produced new furan fatty acid was 7,10-epoxy-octadec-7,9-dienoic acid (7,10-EODA) (see FIG. 5 and Experimental Result 2).

In another general aspect, the present disclosure provides an antioxidant including the 7,10-epoxy-octadeca-7,9-dienoic acid (7,10-EODA). Since the Furan fatty acids are reported to have an antioxidant activity, as described in the Background section, the antioxidant activity of 7,10-EODA of the present disclosure was analyzed by DPPH assay of measuring radical scavenging activity. As a result, 7,10-EODA showed a radical scavenging activity increasing in a dose-dependent manner. Although the activity was lower than that of α-tocopherol or ascorbic acid, 7,10-EODA showed a clear radical scavenging activity in a dose-dependent manner (see FIG. 8). Accordingly, the furan fatty acid according to the present disclosure can be applied in various industrial fields as antioxidant having an antioxidant activity.

DETAILED DESCRIPTION OF THE INVENTION

Figure 1:
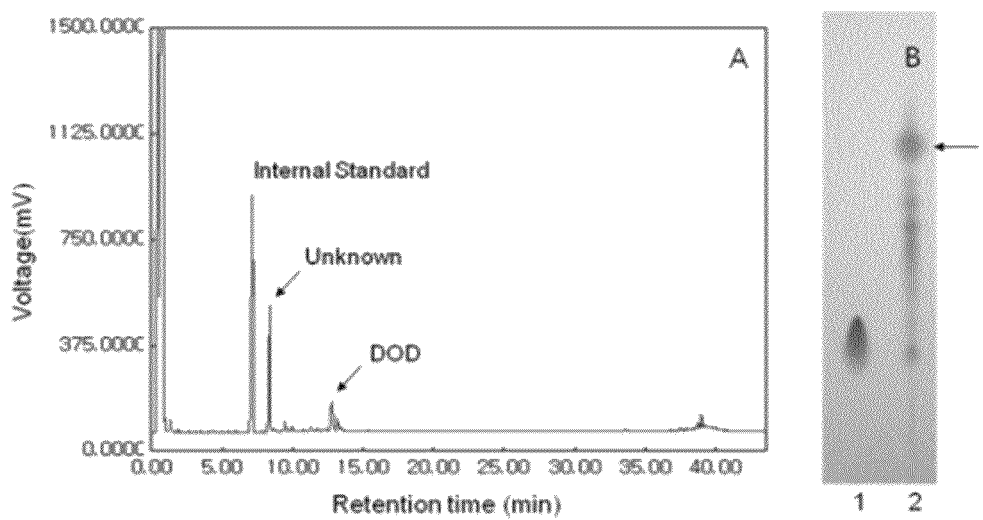
FIG. 1. Analysis of the crude extract obtained from conversion of DOD by heat treatment. Analysis was carried out by GC (A) and TLC (B). Major unknown compound in GC analysis is indicated by the arrow in TLC analysis. Lane 1; standard DOD, lane 2; crude extract of the heat-treated DOD. Other experimental conditions were given in materials and methods section.

The examples and experiments will now be described. The following examples and experiments are for illustrative purposes only and not intended to limit the scope of this disclosure.

Materials

Olive oil (extra virgin grade) was purchased from local market in Korea. Heptadecanoic acid (C17:0) was purchased from Nu-Chek Prep (Elysian Minn., USA). A mixture of trimethylsilylimidazole (TMSI) and pyridine (1:4, v/v) was purchased from Supelco (Bellefonte, Pa. USA). Thin-layer precoated Kieselgel 60F$_{254}$ plates were obtained from EM Science (Cherry Hill, N.J., USA). Silica gel, Davisil™, grade 635, 60-100 mesh, 60A, 99$^+$% and other chemicals were purchased from Sigma-Aldrich (St. Louis, Mo., USA) unless mentioned elsewhere. All other chemicals were reagent grade and were used without further purification.

Example 1

Production of DOD 7,10-dihydroxy-8(E)-octadecenoic acid (DOD) was produced according to our previous report (21). In brief, olive oil (1%, v/v) was added as a substrate to the 24 hr-old culture of *Pseudomonas aeruginosa* PR3 which was cultivated aerobically at 28° C., 200 rpm in shaking incubator followed by an additional 72 hr incubation. Crude DOD extract obtained by extraction of the culture with an equal volume of ethyl acetate was applied to the silica-gel column (1.5 cm I.D.×30 cm) for purification. Fractionation was conducted with two column volumes of the solvent mixture with varied ratio of ethyl acetate over hexane.

Example 2

Production of EODA from DOD by Heat Treatment

Conversion of DOD by heat treatment was carried out in 4 ml glass vial containing 10 mg DOD and 500 µl hexane as solvent. The mixture was incubated at 90° C. for 24 hours on a heating block (Barnstead/Thermolyne Type 176000 Dri-Bath). At the end of the treatment, solvent was evaporated using nitrogen flushing and the reaction product was dissolved in the mixture of chloroform and methanol (1:1, v/v). For the study of time-coursed production, vials containing 10 mg of DOD were heated at 90° C. and withdrawn for analysis after a given time.

Example 3

Analysis of Reaction Products

Reaction products were analyzed by TLC and quantified by GC analysis with heptadecanoic acid being an internal standard. The TLC analysis was developed in a solvent system (toluene:1,4 dioxane:acetic acid, 79:14:7, v/v/v) and the spots were visualized by spraying the plate with 50% sulfuric acid followed by heating at 95° C. for 10 minutes. For GC analysis, the sample methylated with diazomethane for 5 min at room temperature was analyzed with ACME 6100 Series Gas Chromatography System (Younlin Co., Korea) equipped with a flame-ionization detector and a capillary column (SPB-1™, 15 m×0.32 mm i.d., 0.25 µm thickness, Supelco Inc., Bellefonte, Pa., USA). GC was run with a temperature gradient of 20° C./min from 100 to 150° C., 5° C./min from 150 to 200° C., and then 0.5° C./min from 200 to 210° C. followed by holding for 10 min at 300° C. (nitrogen gas flow rate=0.67 ml/min). Injector and detector temperatures were held at 270 and 280° C., respectively.

Chemical structure of the purified target product was determined by GC/MS, NMR, FTIR. Electron-impact (EI) mass spectra was obtained with a Hewlett Packard 5890 GC (Avondale, Pa., USA) coupled to a Hewlett Packard 5972 Series Mass Selective Detector. The column outlet was connected directly to the ion source. Separation was carried out in a methylsilicone column (30 m×0.25 mm i.d., 0.25 □m film thickness) with a temperature gradient of 20° C./min from 70 to 170° C., holding for 1 min at 170° C. and 5° C./min up to 250° C. followed by holding for 15 minutes (helium flow rate=0.67 ml/min). $^1$H-NMR and $^{13}$C-NMR spectra were determined in deuterated chloroform with a Varian-500 spectrometer (Billerica, Mass., USA), operated at a frequency of 400 and 100 MHz, respectively. FTIR analysis of the purified compound was run as films on KBr on a Perkin Elmer Infrared Fourier Transform Model 1750 spectrometer (Perkin Elmer, Oakbrook, Ill., USA).

Antioxidant activity was analyzed using 2,2-Diphenyl-1-picryhydrazyl (DPPH) assay according to the reports (22). Briefly, 50 µl of sample solution in DMSO was added to 200 µl of 200 µM DPPH radical solution in a 96-well plate. L-ascorbic acid and α-Tocopherol were used as positive controls. After 30 min of incubation at 37° C., the absorbance at 515 nm was measured. DPPH free radical scavenging activities was calculated using the equation; radical scavenging activity (%)=$[1-(A_{sample}-A_{blank})/(A_{control}-A_{blank})]\times 100$. DMSO was used as a control.

Experimental Result 1

Production and Isolation of Major Product

Figure 2:
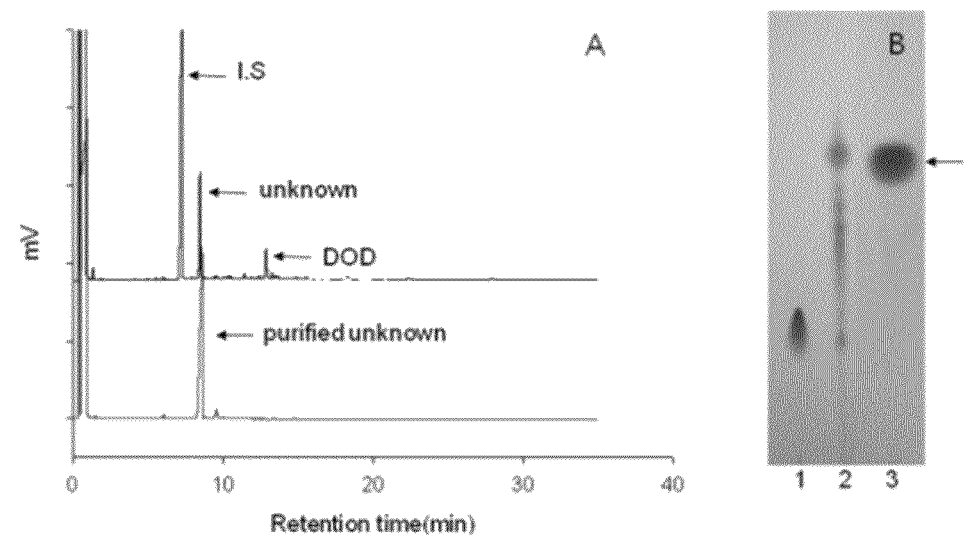
FIG. 2. Analysis of the crude extract and the purified unknown compound obtained from conversion of DOD by heat treatment. Analysis was carried out by GC (A) and TLC (B). Upper and lower GC chromatogram represented crude extract and purified samples, respectively. Major unknown compound in GC analysis is indicated by the arrow in TLC analysis. Lane 1; standard DOD, lane 2; crude extract of the heat-treated DOD, lane 3; purified unknown compound. Other experimental conditions were given in materials and methods section.

Heat treatment of DOD in hexane at 90° C. for 24 hours yielded a mixture of several products including one major product, which were analyzed by TLC (Rf=7.2, FIG. 1, B) and GC (peak retention time=8.2-8.4 min, FIG. 1, A). The major product was purified using a silica-gel column. The target compound (unknown) was obtained from the fraction of hexane:ethyl acetate (8:2, v/v). The purified product with white crystal-like powder was identified as a single major peak with 96% or higher purity by GC (FIG. 2, A) and as one major spot on TLC analysis (FIG. 2, B).

Experimental Result 2

Structure Determination

Figure 3:
FIG. 3. Electron-impact mass spectrum of the methylated unknown compound in FIG. 2. Major fragments were indicated by the arrow. Analytical conditions are explained in materials and methods section.

The purified target product was subjected to GC/MS, FTIR and NMR analysis for structure determination. The electron-impact GC/MS spectrum and the corresponding proposed structure of the methylated product are shown in FIG. 3. The mass spectra of the purified product were characterized by six major peaks in the fragmentogram. Beta-cleavage at both sides of the furan ring yielded a furan fragment at 95 m/z, and intense peaks at 193 m/z and 209 m/z represented the ions formed by beta-cleavage of the furanoid ring toward the methyl and the methylated carboxyl end, respectively. Evidence of the loss of a methoxy group was seen at 277 m/z. This GC/MS analysis result was in close agreement with that of the chemically synthesized 9,12-epoxy-octadeca-9,11-dienoic acid, except the location of the furan ring being two carbons farther from the carboxyl group (23).

Based on the GC-MS analysis result, the structure of the target product was expected as shown in FIG. 3. As seen in the figure, the furanoid fatty acid was expected to include an epoxy structure connected by an oxygen atom between carbon 7 and 10 and have two double bonds between carbon 7 and 8 and between carbon 9 and 10. The GC-MS spectrum was in perfect agreement with the structure expected from the fragment pattern.

Most of the naturally-occurring furanoid fatty acids are found in trace amounts in fish. Mostly, the furan ring is substituted by one or two methyl residues. The length of the side chain is various. It is also known to be contained in human blood in trace quantity. However, one with no methyl residue is not known to occur naturally and it is reported that a small amount can be produced as intermediate when linoleic acid is treated with lipoxygenase. However, the resulting furanoid fatty acid is different in the position of the furan ring from that provided by the present disclosure. That is to say, it has an epoxy structure carbon 10 and 13.

As described, the novel furanoid fatty acid presented in the present disclosure is a new substance that has never been reported. Therefore, the inventors performed further structural analysis by NMR and FTIR.

Figure 4:
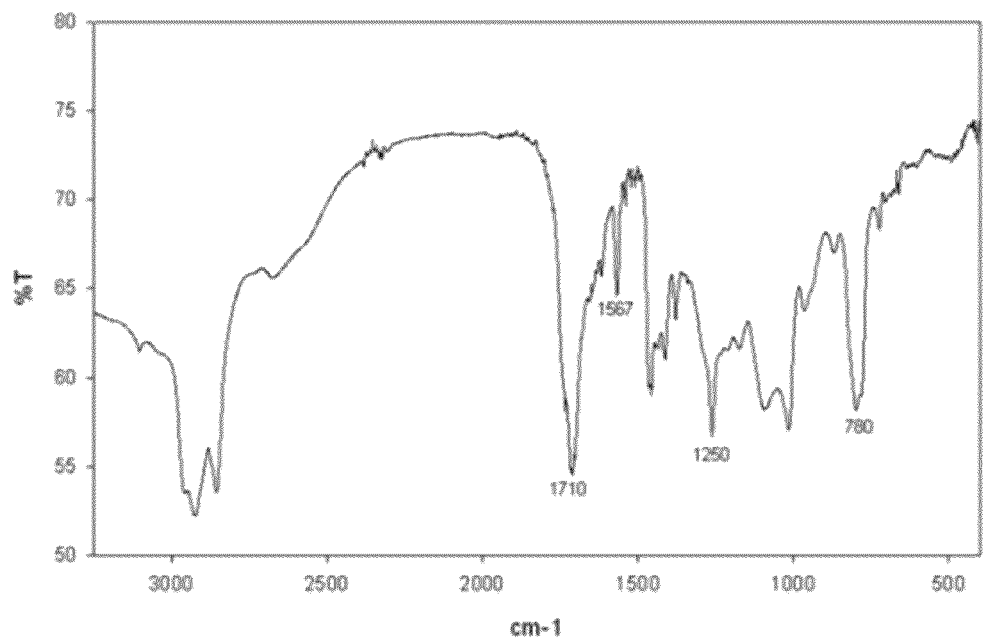
FIG. 4. FTIR analysis of the purified 7,10-EODA. Analytical conditions are explained in materials and methods section.
Figure 5:
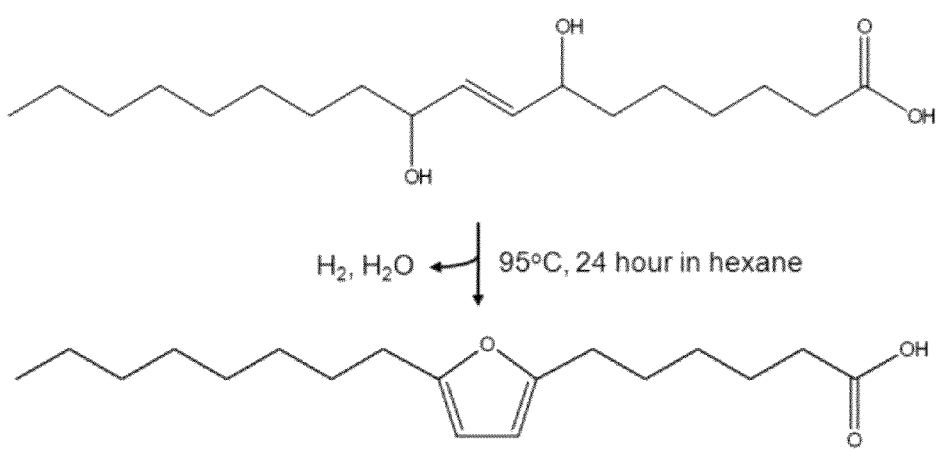
FIG. 5. Schematic pathway for conversion of DOD by heat treatment leading to the formation of 7,10-EODA.

FTIR analysis presented several characteristic absorptions at 1710 (carbonyl), 780 (out of plane $\delta$CH), 1250 (in plane $\delta$CH) and 1567 (C=C, furan) cm$^{-1}$ (FIG. 4). The overall absorption pattern was in close agreement with data on synthetic furan molecules reported by other workers (24). NMR analysis confirmed the elucidated structure of the purified product. Resonance signals (ppm) and corresponding molecular assignments were as follows; $^1$H-NMR (400 MHz, CDCl$_3$): 2.34 (2H, CH$_2$COOH), 5.84 (2H, furan), 2.57 (4H, 2×CH$_2$-furan), 0.89 (3H, CH$_3$), 1.28-1.61 (18H, 9×—CH$_2$—). $^{13}$C-NMR (100 MHz, CDCl$_3$) analysis confirmed the presence of a furan ring at 104.81, 105.02, 154.09 and 154.81 (C7, C8, C9 and C10, respectively), —CH$_3$ at 14.11 (C18), and carboxyl carbon at 178.64 (C1). Other carbons were at 33.78 (C2), 24.45 (C3), 27.22 (C4), 29.71 (C5), 33.78 (C6), 31.87 (C11), 29.35 (C12), 27.84 (C13), 28.58 (C14), 29.24 (C15), 31.94 (C16) and 22.67 (C17). The data from the GC-MS, FTIR and NMR analyses confirmed that the purified product was 7,10-epoxy-octadeca-7,9-dienoic acid with a molecular weight of 294 (molecular weight was identified by GC/MS analysis) (FIG. 5). Based on the structure, the compound was named as 7,10-EODA.

Chemical synthesis of a furan fatty acid without a substituent was first reported by Lie Ken Jie et al. They reported that some fatty acids containing isomeric C$_{18}$ furans were chemically synthesized from furan through complicated multiple steps using several catalysts (24). Alaiz et al. also reported that 9,12-epoxy-octadeca-9,11-dienoic acid was synthesized from ricinoleic acid through several chemical steps using chemical catalysts (25). However, in the present disclosure, no chemical catalyst was used. Instead, a single heat-treatment step was enough to produce the novel furan fatty acid from DOD. This is the first report of one-step synthesis of a novel furan fatty acid from DOD by heat treatment. Through database search (NIST MS Search 2.0 and Cambridge Soft Chem Office ver. 5), the inventors of the present disclosure validated that EODA was a newly synthesized furan fatty acid. Comparison with other F-acids revealed no information about the compound of the present disclosure.

Experimental Result 3

Time-Coursed Production and Antioxidant Activity

Figure 6:
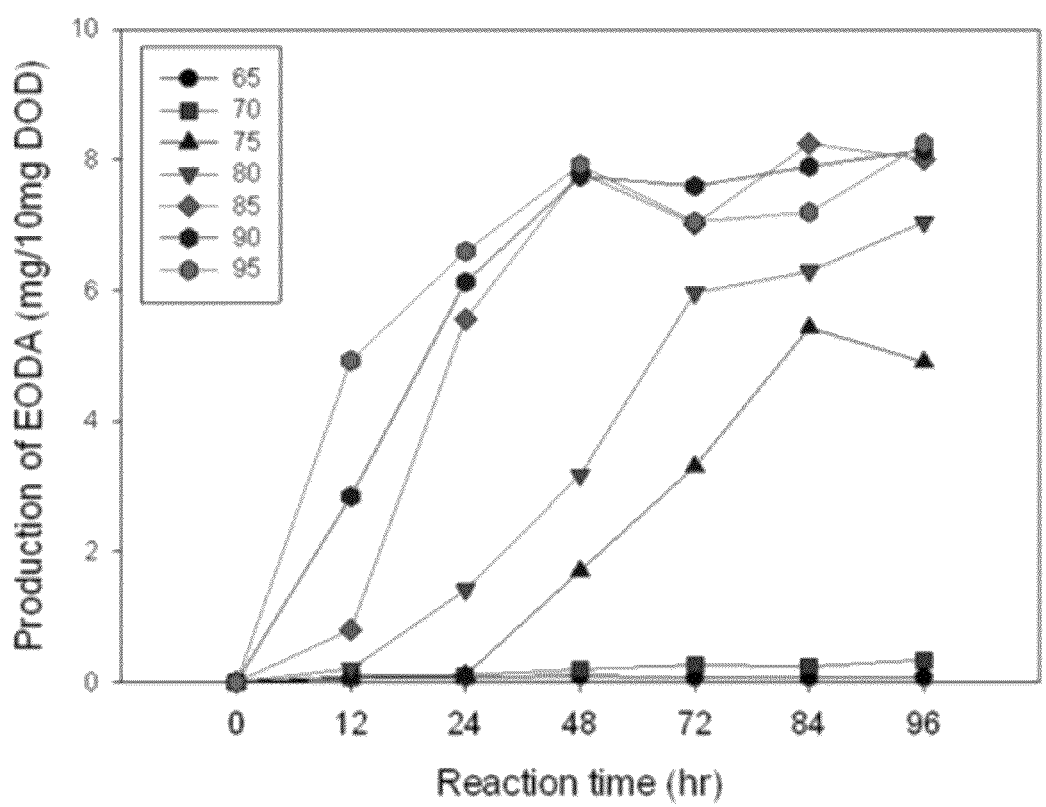
FIG. 6. Reaction temperature-coursed production of 7,10-EODA.

EODA was produced in the same manner as in Example 2. The production of EODA was monitored while varying the reaction temperature (see FIG. 6). As seen from FIG. 6, the production of EODA increased as the reaction temperature was higher and as the reaction time was longer. The maximum production yield was about 80%. It was confirmed that, to achieve the maximum production yield, the reaction temperature should be maintained at 85° C. or higher and the reaction time should be about 48 hours.

Figure 7:
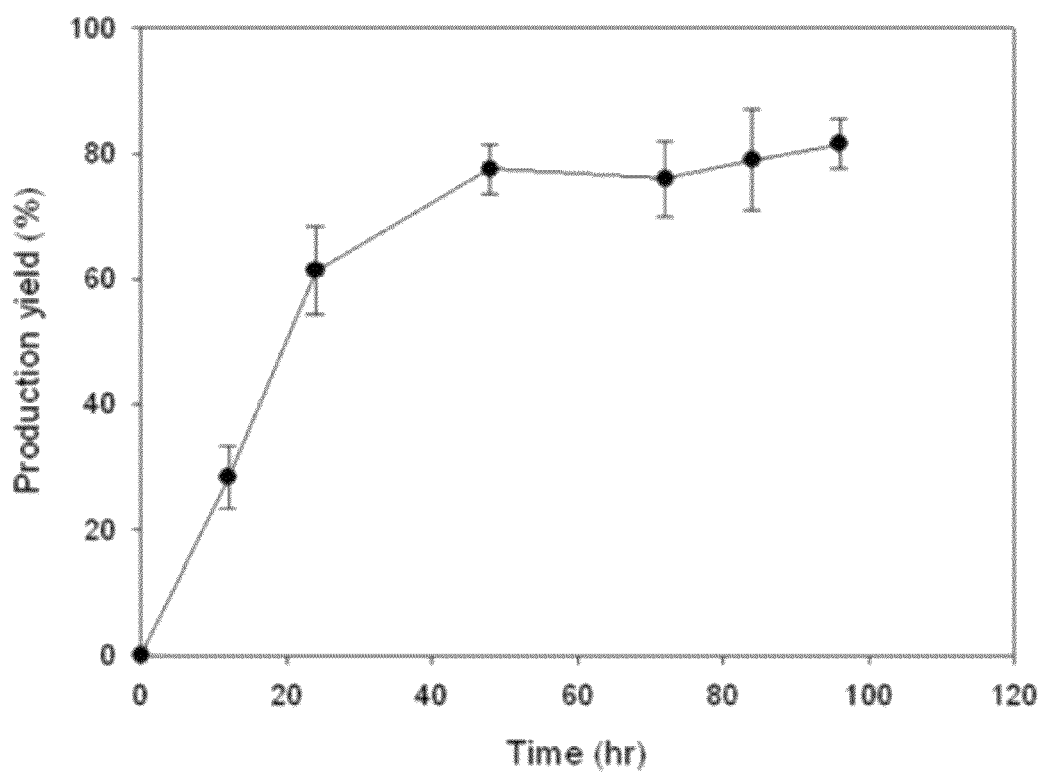
FIG. 7. Time-coursed production of 7,10-EODA. Experimental conditions were given in materials and methods section.

Thus, the time-coursed production of 7,10-EODA was studied for 96 hours at 90° C. As seen from FIG. 7, the production of 7,10-EODA increased proportionally with time up to 48 hours and reached plateau thereafter. The maximum production yield under this condition was 82%.

Figure 8:
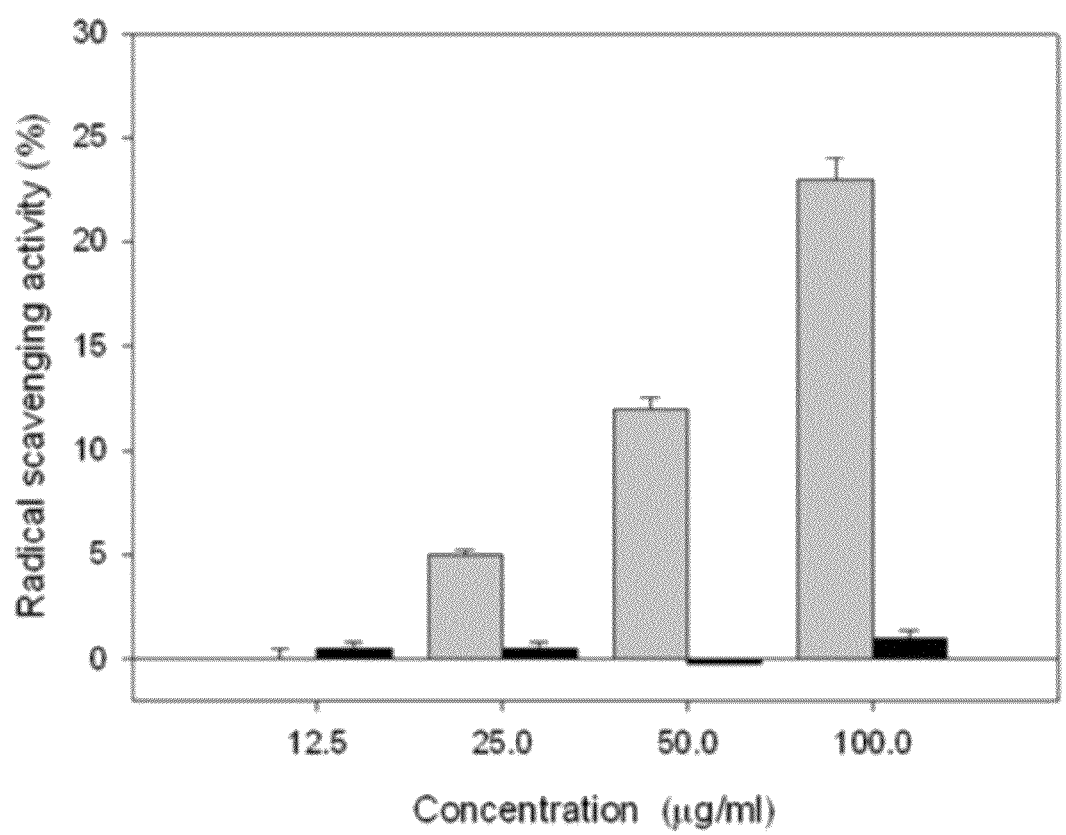
FIG. 8. Radical scavenging activity of the purified 7,10-EODA. Black and gray bars represented 7,10-EODA and DOD, respectively. Analytical conditions are explained in materials and methods section.

Since furan fatty acids have been reported to have antioxidant activity, the antioxidant activity of 7,10-EODA was determined by DPPH assay as radical scavenging activity and compared to that of DOD (FIG. 8). The radical scavenging activity of 7,10-EODA increased dose-dependently, presenting 23% at the highest concentration (100 μg/mL) tested, while DOD did not show any activity. Although the activity was relatively low when compared to that of α-tocopherol or ascorbic acid, 7,10-EODA showed a clear radical scavenging activity in a dose-dependent manner. This finding confirmed the previous assumptions that F-acids exhibit antioxidant activity. Furan fatty acids are strong scavengers of hydroxyl radicals, inhibit erythrocyte hemolysis induced by singlet oxygen, and are found exclusively at the sn1 position of phosphatidylcholine (26). Diet-derived F-acids are incorporated into the tissue and blood of mammals, especially into phospholipids where they partly substitute for polyunsaturated fatty acids (PUFA) (27). Based on these biochemical and biological studies of F-acids, it is considered that F-acids are critically important antioxidant materials for mammals including human. Hence, new finding of a simple way for cost-effective production of F-acid is meaningful.

To conclude, the present disclosure provides a simple method for producing 7,10-EODA from a dihydroxyl fatty acid precursor. Considering the difficulties in purifying natural furan fatty acids because of easy attack by peroxyl radicals and small quantity and the complicated multiple steps for chemical synthesis, the present disclosure provides a useful way to produce the biologically activity F-acid cost-effectively in large scale.

As described, the present disclosure allows production of a new biologically active furan fatty acid through a one-step heat-treatment process of 7,10-dihydroxy-8(E)-octadecenoic acid prepared from vegetable oil by microbial conversion. Considering the difficulties in purifying natural furan fatty acids because of easy attack by peroxyl radicals and small quantity and the complicated multiple steps for chemical synthesis, the present disclosure provides a useful way to produce the biologically activity F-acid cost-effectively in large scale.

While the present disclosure has been described with respect to the specific embodiments, it will be apparent to those skilled in the art that various changes and modifications may be made without departing from the spirit and scope of the disclosure as defined in the following claims.

LITERATURE CITED (1) Glass, R. L.; Krick, T. P.; Sand, D. M.; Rahn, C. H.; Schlenk, H. Furanoid Fatty Acids from Fish Lipids. *Lipids,* 1975, 10, 695-702.
(2) Morris, L. J.; Marshall, M. O.; Kelly, W. A Unique Furanoid Fatty Acid from Exocarpus seed oil. *Tetrahedron Lett.* 1966, 16, 4249-4253.
(3) Glass, R. L.; Krick, T. P.; Eckhardt, A. E. New Series of Fatty Acids in Northern Pike (Esox Indus). *Lipids,* 1974, 9, 1004-1008.
(4) Gunstone, F. D.; Wijesundera, R. C.; Scrimgeour, C. M. The Component Acids of Lipids from Marine and Freshwater Species with Special Reference to Furan-Containing Acids. *J. Sci. Food Agric.* 1978, 29, 539-550.
(5) Hannemann, K.; Puchta, V.; Simon, E.; Ziegler, H.; Ziegler, G.; Spiteller, G. The Common Occurrence of Furan Fatty Acids in Plants. *Lipids,* 1989, 24, 296-298.
(6) Ishii, K.; Okajima, H.; Okada, Y.; Watanabe, H. Studies on Furan Fatty Acids of Salmon Roe Phospholipids. *J. Biochem. (Tokyo),* 1988, 103, 836-839.
(7) Ota, T.; Takagi, T. Furan Fatty Acids in the Lipids of the Cresthead Flounder. *Nippon Suisan Gakkaishi,* 1992, 58, 721-725.

(8) Ishii, K.; Okajima, H.; Okada, Y.; Watanabe, H. Effects of Phosphatidylcholines Containing Furan Fatty Acid on Oxidation in Multilamellar Liposomes. *Chem. Pharm. Bull.* 1989, 37, 1396-1398.

(9) Graft, G.; Gellerman, J. L.; Sand, D. M.; Schlenk, H. Inhibition of Blood Platelet Aggregation by Dioxo-ene Compounds. *Biochim. Biophys. Acta*, 1984, 799, 143-150.

(10) Okada, Y.; Kaneko, M.; Okajima, H. Hydroxy Radical Scavenging Activity of Naturally Occurring Furan Fatty Acids. *Biol. Pharm. Bull.* 1996, 19, 1607-1610.

(11) Glass, R. L.; Krick, T. P.; Olson, D. L.; Thorson, R. L. The Occurrence and Distribution of Furan Fatty Acids in Spawning Male Freshwater Fish. *Lipids,* 1977, 12, 828-836.

(12) Spiteller, G. Furan fatty acids: Occurrences, synthesis, and reactions. Are furan fatty acids responsible for the cardioprotective effects of a fish diet? *Lipids,* 2005, 40, 755-771.

(13) Okada, Y.; Okajima, H.; Konishi, H.; Terauchi, M.; Ishii, K.; Liu, I. M.; Watanabe, H. Antioxidant Effect of Naturally Occurring Furan Fatty Acids on Oxidation of Linoleic Acid in Aqueous Dispersion. *J. Am. Oil Chem. Soc.* 1990, 67, 858-862.

(14) Batna, A.; Spiteller, G. Oxidation of Furan Fatty Acids by Soybean Lipoxygenase-1 in the Presence of Linoleic Acid. *Chem. Phys. Lipids,* 1994, 70, 179-185.

(15) Jandke, J.; Schmidt, J.; Spiteller G. Über das Verhalten von F-Sauren bei der Oxidation mit Lipoxydase in Anwesenheit von SH-haltigen Verbindungen, liebigs *Ann. Chem.* 1988, 29-34.

(16) Schödel, R.; Spiteller, G. Uber die Strukturaufklärung von (Hydroxy-oxo-cyclopentenyl) alkansauren, den Aldolkondensationsprodukten von Dioxoen carbonsäuren aus Rinderleber. *Helv. Chim. Acta,* 1985, 68, 1624-1634.

(17) Fuchs, C.; Spiteller, G. Iron Release from the Active Site of Lipoxygenase, Z. *Naturforsch.* 2000, 55, 643-648

(18) Halliwell, B.; Gutteridge, J. M. C. Role of Free Radicals and Catalytic Metal Ions in Human Disease: An Overview, *Methods Enzymol.* 1990, 186, 1-85.

(19) Scheinkonig, J.; Hannemann, K.; Spiteller, G. Methylation of the β-Positions of the Furan Ring in F-Acids. *Biochim. Biophys. Acta,* 1995, 1254, 73-76.

(20) Puchta, V.; Spiteller, G.; Weidinger, H. F-Säuren: Eine bisher unbekannte Komponente der Phospholipide des Humanblutes, *Liebigs Ann. Chem.* 1988, 25-28.

(21) Chang, I. A.; Kim, I. H.; Kang, S. C.; Hou, C. T.; Kim, H. R. Production of 7,10-dihydroxy-8(E)-octadecenoic acid from triolein via lipase induction by *Pseudomonasa eruginosa* PR3. *Appl. Microbiol. Biotechnol.* 2007, 74, 301-306.

(22) Tepe, B.; Daferera, D.; Tepe, A. S.; Polissiou, P.; Sokmen, A. Antioxidant activity of the essential oil and various extracts of *Nepeta flavida* Hub-Mor from Turkey. *Food Chem.* 2007, 103, 1358-1364

(23) Lie Ken Jie, M. S. F.; Wong, K. P. A Novel method for the introduction of a methyl group into the furan ring of a 2,5-disubstituted $C_{18}$ furanoid fatty ester via a malonic acid function. *Lipids,* 1991, 26, 837-842.

(24) Lie Ken Jie, M. S. F.; Lam, C. H. Fatty acids: Part XVI. The synthesis of all isomeric $C_{18}$ furan-containing fatty acids. *Chem. Phys. Lipids,* 1978, 21, 275-287.

(25) Alaiz, M.; Hidalgo, F. J.; Zamora, R.; Millan, F.; Maza, M. P.; Vioque, E. Synthesis of 9,12-epoxy octadeca-9,11-dienoic acid. *Chem. Phys. Lipids,* 1988, 48, 289-292.

(26) White, D. C.; Geyer, R.; Peacock, A. D.; Hedrick, D. B.; Koenigsberg, S. S.; Sung, Y.; He, J.; Loffler, F. E. Phospholipid furan fatty acids and ubiquinone-8:lipids biomarkers that may protect *Dehalococcoides* strains from free radicals. *Appl. Environ. Microbiol.* 2005, 8426-8433.

(27) Wahl, H. G.; Chrzanowski, A.; Millier, C.; liebich, H. M.; Hoffmann, A. Identification of Furan Fatty Acids in Human Blood Cells and Plasma by Multi-dimensional Gas Chromatography-Mass Spectrometry. *J. Chromatogr. A* 1995, 697, 453-459.

What is claimed is:

1. A method for preparing a furan fatty acid, comprising:
   mixing 7,10-dihydroxy-8(E)-octadecenoic acid (DOD) with hexane; and
   heat-treating the resulting mixture.

2. The method for preparing a furan fatty acid according to claim 1, wherein the 7,10-dihydroxy-8(E)-octadecenoic acid is produced by the microorganism *Pseudomonas aeruginosa* using oleic acid or vegetable oil containing oleic acid as substrate.

3. The method for preparing a furan fatty acid according to claim 2, wherein the vegetable oil is selected from a group consisting of olive oil, safflower seed oil, soybean oil, corn oil, sesame oil, perilla oil, grape seed oil, hot pepper seed oil, canola oil, sunflower oil, Korean melon seed oil, rapeseed oil and rice bran oil.

4. The method for preparing a furan fatty acid according to claim 2, wherein the microorganism is *Pseudomonas aeruginosa* PR3 (NRRL strain B-18602).

5. The method for preparing a furan fatty acid according to claim 1, wherein 10-1000 µL of hexane is mixed per 10 mg of DOD.

6. The method for preparing a furan fatty acid according to claim 1, wherein the heat treatment is performed at 30-150° C. for 1-150 hours.

7. 7,10-Epoxy-octadeca-7,9-dienoic acid prepared by heat-treating 7,10-dihydroxy-8(E)-octadecenoic acid (DOD) in hexane.

8. An antioxidant comprising the 7,10-epoxy-octadeca-7,9-dienoic acid according to claim 7.

\* \* \* \* \*